(12) United States Patent
Lo et al.

(10) Patent No.: US 6,258,540 B1
(45) Date of Patent: Jul. 10, 2001

(54) NON-INVASIVE PRENATAL DIAGNOSIS

(75) Inventors: Yuk-Ming Dennis Lo, Kowloon (CN); James Stephen Wainscoat, Oxford (GB)

(73) Assignee: Isis Innovation Limited, Oxford (GB)

( * ) Notice: Subject to any disclaimer, the term of this patent is extended or adjusted under 35 U.S.C. 154(b) by 0 days.

(21) Appl. No.: 09/380,696

(22) PCT Filed: Mar. 4, 1998

(86) PCT No.: PCT/GB98/00690

§ 371 Date: Nov. 29, 1999

§ 102(e) Date: Nov. 29, 1999

(87) PCT Pub. No.: WO98/39474

PCT Pub. Date: Sep. 11, 1998

(30) Foreign Application Priority Data

Mar. 4, 1997 (GB) .................................................. 9704444

(51) Int. Cl.$^7$ ...................................................... C12Q 1/68
(52) U.S. Cl. ........................... 435/6; 435/91.2; 435/91.5; 435/440
(58) Field of Search .............................. 435/6, 91.2, 440, 435/91.5

(56) References Cited

FOREIGN PATENT DOCUMENTS

| 2299166 | 9/1996 | (GB) | C12Q/1/68 |
| 9108304 | 6/1991 | (WO) | C12Q/1/68 |
| 9506137 | 3/1995 | (WO) | C12Q/1/68 |

OTHER PUBLICATIONS

Anucucci et al. "Prenatl diagnosis of Myotonic Dystrophy using fetal DNA obtained from maternal plasma" Clinical Chemistry, vol. 46, pp. 301–302, Feb. 2000.*

Bischoff et al "Noninvasive Determination of Fetal RhD status using fetal DNA in Maternal Serum and PCR" J. of the Society for gynecologic investigation, vol. 6, No. 2, pp. 64–69, Mar.–Apr. 2000.*

Journal of Immunological Methods; vol. 180, No. 1; Fowke et al.; "Genetic Analysis of Human DNA Recovered From Minute Amounts of Serum or Plasma"; Mar. 1995; pp 45–51; XP004021069.

Database Medline; US National Library of Medicine (NLM); Bethesda, MD, US; Lo et al.; "Presence of Fetal DNA in Maternal Plasma and Serum"; AN (NLM) 97420079; XP002070361; See also Lancet, Aug. 1997; 350 (9076) pp 485–487, England.

Tsitologia; vol. 37, No. 3; Kazakov et al.; "Extracellular DNA in the Blood of Pregnant Women"; 1995; Institute of Cytology, Russian Academy of Sciences, and Medical Academy of Post Graduate Education, St. Petersburg; pp 1–8.

Lo et al "Presence of fetal DNA in maternal plasma and serum" Lancet, vol. 350, pp. 485–487, Aug. 1997.*

Lo "Fetal RhD genotyping from maternal plasma" Annals of Medicine, vol. 31, No. 5, pp. 308–3012, Oct. 1999.*

Bianchi "Fetal DNA in Maternal Plasma: The plot thickens and the placental barrier thins" Am. J. Hum. Genet. vol. 62, pp. 763–764, Apr. 1998.*

Lo et al "Prenatal Diagnosis of Fetal RhD status by molecular analysis of maternal plasma" New England J. of Med. vol. 339, No. 24, pp. 1734–1738, Dec. 1998.*

* cited by examiner

Primary Examiner—Lisa B. Arthur
Assistant Examiner—Jeanine Goldberg
(74) Attorney, Agent, or Firm—Volpe and Koenig, P.C.

(57) ABSTRACT

The invention relates to a detection method performed on a maternal serum or plasma sample from a pregnant female, which method comprises detecting the presence of a nucleic acid of foetal origin in the sample. The invention enables non-invasive prenatal diagnosis including for example sex determination, blood typing and other genotyping, and detection of pre-eclampsia in the mother.

27 Claims, 4 Drawing Sheets

SEQUENCE LISTING

```
<160> NUMBER OF SEQ ID NOS: 11

<210> SEQ ID NO 1
<211> LENGTH: 21
<212> TYPE: DNA
<213> ORGANISM: Artificial Sequence
<220> FEATURE:
<223> OTHER INFORMATION: GeneAmp DNA Amplification Primer Y1.7

<400> SEQUENCE: 1
catccagagc gtccctggct t                                        21

<210> SEQ ID NO 2
<211> LENGTH: 21
<212> TYPE: DNA
<213> ORGANISM: Artificial Sequence
<220> FEATURE:
<223> OTHER INFORMATION: GeneAmp DNA Amplification Primer Y1.8

<400> SEQUENCE: 2
ctttccacag ccacatttgt c                                        21

<210> SEQ ID NO 3
<211> LENGTH: 21
<212> TYPE: DNA
<213> ORGANISM: Artificial Sequence
<220> FEATURE:
<223> OTHER INFORMATION: TaqMan Amplification Primer SRY-109F

<400> SEQUENCE: 3
tggcgattaa gtcaaattcg c                                        21

<210> SEQ ID NO 4
<211> LENGTH: 25
<212> TYPE: DNA
<213> ORGANISM: Artificial Sequence
<220> FEATURE:
<223> OTHER INFORMATION: TaqMan Amplification Primer SRY-245R

<400> SEQUENCE: 4 cccctagta ccctgacaat gtatt                                     25

<210> SEQ ID NO 5
<211> LENGTH: 26
<212> TYPE: DNA
<213> ORGANISM: Artificial Sequence
<220> FEATURE:
<223> OTHER INFORMATION: Dual Labeled Fluorescent TaqMan Probe SRY-142T

<400> SEQUENCE: 5
agcagtagag cactcaggga ggcaga                                   26

<210> SEQ ID NO 6
<211> LENGTH: 21
<212> TYPE: DNA
<213> ORGANISM: Artificial Sequence
```

```
<220> FEATURE:
<223> OTHER INFORMATION: RhD TaqMan Amplification Primer RD-A

<400> SEQUENCE: 6
cctctcactg ttgcctgcat t                                              21

<210> SEQ ID NO 7
<211> LENGTH: 18
<212> TYPE: DNA
<213> ORGANISM: Artificial Sequence
<220> FEATURE:
<223> OTHER INFORMATION: RhD TaqMan Amplification Primer RD-B

<400> SEQUENCE: 7
agtgcctgcg cgaccatt                                                  18

<210> SEQ ID NO 8
<211> LENGTH: 31
<212> TYPE: DNA
<213> ORGANISM: Artificial Sequence
<220> FEATURE:
<223> OTHER INFORMATION: Dual Labelled Fluorescent TaqMan Probe RD-T

<400> SEQUENCE: 8
tacgtgagaa acgctcatga cagcaaagtc t                                   31

<210> SEQ ID NO 9
<211> LENGTH: 22
<212> TYPE: DNA
<213> ORGANISM: Artificial Sequence
<220> FEATURE:
<223> OTHER INFORMATION: TaqMan Amplification Primer beta-globin-354F

<400> SEQUENCE: 9
gtgcacctga ctcctgagga ga                                             22

<210> SEQ ID NO 10
<211> LENGTH: 21
<212> TYPE: DNA
<213> ORGANISM: Artificial Sequence
<220> FEATURE:
<223> OTHER INFORMATION: TaqMan Amplification Primer beta-globin-455R

<400> SEQUENCE: 10
ccttgatacc aacctgccca g                                              21

<210> SEQ ID NO 11
<211> LENGTH: 26
<212> TYPE: DNA
<213> ORGANISM: Artificial Sequence
<220> FEATURE:
<223> OTHER INFORMATION: Dual Labelled Fluorescent TaqMan Probe beta-
      globin-402T

<400> SEQUENCE: 11
aaggtgaacg tggatgaagt tggtgg                                         26
```

NON-INVASIVE PRENATAL DIAGNOSIS

This application is the national stage of PCT Application No. PCT/GB98/00690, filed Mar. 4, 1998 under 37 CFR 371.

This invention relates to prenatal detection methods using non-invasive techniques. In particular, it relates to prenatal diagnosis by detecting foetal nucleic acids in serum or plasma from a maternal blood sample.

BACKGROUND OF THE INVENTION

Conventional prenatal screening methods for detecting foetal abnormalities and for sex determination traditionally use foetal samples derived by invasive techniques such as amniocentesis and chorionic villus sampling. These techniques require careful handling and present a degree of risk to the mother and to the pregnancy.

More recently, techniques have been devised for predicting abnormalities in the foetus and possible complications in pregnancy, which use maternal blood or serum samples. Three markers commonly used include alpha-foetoprotein (AFP—of foetal origin), human chorionic gonadotrophin (hCG) and estriol, for screening for Down's Syndrome and neural tube defects. Maternal serum is also currently used for biochemical screening for chromosomal aneuploidies and neural tube defects. The passage of nucleated cells between the mother and foetus is now a well-recognised phenomenon (Lo et al 1989; Lo et al 1996). The use of foetal cells in maternal blood for non-invasive prenatal diagnosis (Simpson and Elias 1993) avoids the risks associated with conventional invasive techniques. WO 91/08304 describes prenatal genetic determination using foetal DNA obtained from foetal cells in the maternal blood. Considerable advances have been made in the enrichment and isolation of foetal cells for analysis (Simpson and Elias 1993; Cheung et al 1996). However, these techniques are time-consuming or require expensive equipment.

Recently, there has been interest in the use of plasma or serum-derived DNA for molecular diagnosis (Mulcahy et al 1996). In particular, it has been demonstrated that tumour DNA can be detected by the polymerase chain reaction (PCR) in the plasma or serum of some patients (Chen et al 1996; Nawroz et al 1996).

GB 2 299 166 describes non-invasive cancer diagnosis by detection of K-ras and N-ras gene mutations using PCR-based techniques.

SUMMARY AND OBJECTS OF THE INVENTION

It has now been discovered that foetal DNA is detectable in maternal serum or plasma samples. This is a surprising and unexpected finding; maternal plasma is the very material that is routinely discarded by investigators studying non-invasive prenatal diagnosis using foetal cells in maternal blood. The detection rate is much higher using serum or plasma than using nucleated blood cell DNA extracted from a comparable volume of whole blood, suggesting that there is enrichment of foetal DNA in maternal plasma and serum. In fact, the concentration of foetal DNA in maternal plasma expressed as a % of total DNA has been measured as from 0.39% (the lowest concentration measured in early pregnancy), to as high as 11.4% (in late pregnancy), compared to ratios of generally around 0.001% and up to only 0.025% for cellular fractions (Hamada et al 1993). It is important that foetal DNA is found in maternal plasma as well as serum because this indicates that the DNA is not an artefact of the clotting process.

This invention provides a detection method performed on a maternal serum or plasma sample from a pregnant female, which method comprises detecting the presence of a nucleic acid of foetal origin in the sample. The invention thus provides a method for prenatal diagnosis.

The term "prenatal diagnosis" as used herein covers determination of any maternal or foetal condition or characteristic which is related to either the foetal DNA itself or to the quantity or quality of the foetal DNA in the maternal serum or plasma. Included are sex determination, and detection of foetal abnormalities which may be for example chromosomal aneuploidies or simple mutations. Also included is detection and monitoring of pregnancy-associated conditions such as pre-eclampsia which result in higher or lower than normal amounts of foetal DNA being present in the maternal serum or plasma. The nucleic acid detected in the method according to the invention may be of a type other than DNA e.g. mRNA.

The maternal serum or plasma sample is derived from the maternal blood. As little as 10 $\mu$l of serum or plasma can be used. However it may be preferable to employ larger samples in order to increase accuracy. The volume of the sample required may be dependent upon the condition or characteristic being detected. In any case, the volume of maternal blood which needs to be taken is small.

The preparation of serum or plasma from the maternal blood sample is carried out by standard techniques. The serum or plasma is normally then subjected to a nucleic acid extraction process. Suitable methods include the methods described herein in the examples, and variations of those methods. Possible alternatives include the controlled heating method described by Frickhofen and Young (1991). Another suitable serum and plasma extraction method is proteinase K treatment followed by phenol/chloroform extraction. Serum and plasma nucleic acid extraction methods allowing the purification of DNA or RNA from larger volumes of maternal sample increase the amount of foetal nucleic acid material for analysis and thus improve the accuracy. A sequence-based enrichment method could also be used on the maternal serum or plasma to specifically enrich for foetal nucleic acid sequences.

An amplification of foetal DNA sequences in the sample is normally carried out. Standard nucleic acid amplification systems can be used, including PCR, the ligase chain reaction, nucleic acid sequence based amplification (NASBA), branched DNA methods, and so on. Preferred amplification methods involve PCR.

The method according to the invention may be particularly useful for sex determination which may be carried out by detecting the presence of a Y chromosome. It is demonstrated herein that using only 10 $\mu$l of plasma or serum a detection rate of 80% for plasma and 70% for serum can be achieved. The use of less than 1 ml of maternal plasma or serum has been shown to give a 100% accurate detection rate.

The method according to the invention can be applied to the detection of any paternally-inherited sequences which are not possessed by the mother and which may be for example genes which confer a disease phenotype in the foetus. Examples include:

a) Foetal rhesus D status determination in rhesus negative mothers (Lo et al 1993). This is possible because rhesus D positive individuals possess the rhesus D gene which is absent in rhesus D negative individuals. Therefore, the detection of rhesus D gene sequences in the plasma and serum of a rhesus D negative mother is indicative of the presence of a rhesus D positive foetus. This approach may also be applied to the detection of foetal rhesus D mRNA in maternal plasma and serum.

b) Haemoglobinopathies (Camaschella et al 1990). Over 450 different mutations in the beta-globin gene have been known to cause beta-thalassaemia. Provided that the father and mother carry different mutations, the paternal mutation can be used as an amplification target on maternal plasma and serum, so as to assess the risk that the foetus may be affected.

c) Paternally-inherited DNA polymorphisms or mutations. Paternally-inherited DNA polymorphisms or mutations present on either a Y or a non-Y chromosome, can be detected in maternal plasma and serum to assess the risk of the foetus being affected by a particular disease by linkage analysis. Furthermore, this type of analysis can also be used to ascertain the presence of foetal nucleic acid in a particular maternal plasma or serum sample, prior to diagnostic analysis such as sex determination. This application will require the prior genotyping of the father and mother using a panel of polymorphic markers and then an allele for detection will be chosen which is present in the father, but is absent in the mother.

The plasma or serum-based non-invasive prenatal diagnosis method according to the invention can be applied to screening for Down's Syndrome and other chromosomal aneuploidies. Two possible ways in which this might be done are as follows:

a) It has been found that in pregnancy involving foetuses with chromosomal aneuploidies e.g. Down's Syndrome, the level of foetal cells circulating in maternal blood is higher than in pregnancies involving normal foetuses (Bianchi et al 1996). Following the surprising discovery disclosed herein that foetal DNA is present in maternal plasma and serum, it has also been demonstrated that the level of foetal DNA in maternal plasma and serum is higher in pregnancies where the foetus has a chromosomal aneuploidy than in normal pregnancies. Quantitative detection of foetal nucleic acid in the maternal plasma or serum e.g. a quantitative PCR assay, can be used to screen pregnant women for chromosomal aneuploidies.

b) A second method involves the quantitation of foetal DNA markers on different chromosomes. For example, for a foetus affected by Down's Syndrome the absolute quantity of foetal chromosomal 21-derived DNA will always be greater than that from the other chromosomes. The recent development of very accurate quantitative PCR techniques, such as real time quantitative PCR (Heid et al 1996) facilitates this type of analysis.

Another application of the accurate quantitation of foetal nucleic acid levels in the maternal serum or plasma is in the molecular monitoring of certain placental pathologies, such as pre-eclampsia. The concentration of foetal DNA in maternal serum and plasma is elevated in pre-eclampsia. This is probably due to the placental damage which occurs.

It is anticipated that it will be possible to incorporate the nucleic acid-based diagnosis methods described herein into existing prenatal screening programmes. Sex determination has successfully been performed on pregnancies from 7 to 40 weeks of gestation.

DETAILED DESCRIPTION OF THE PREFERRED EMBODIMENTS

Figure 1:
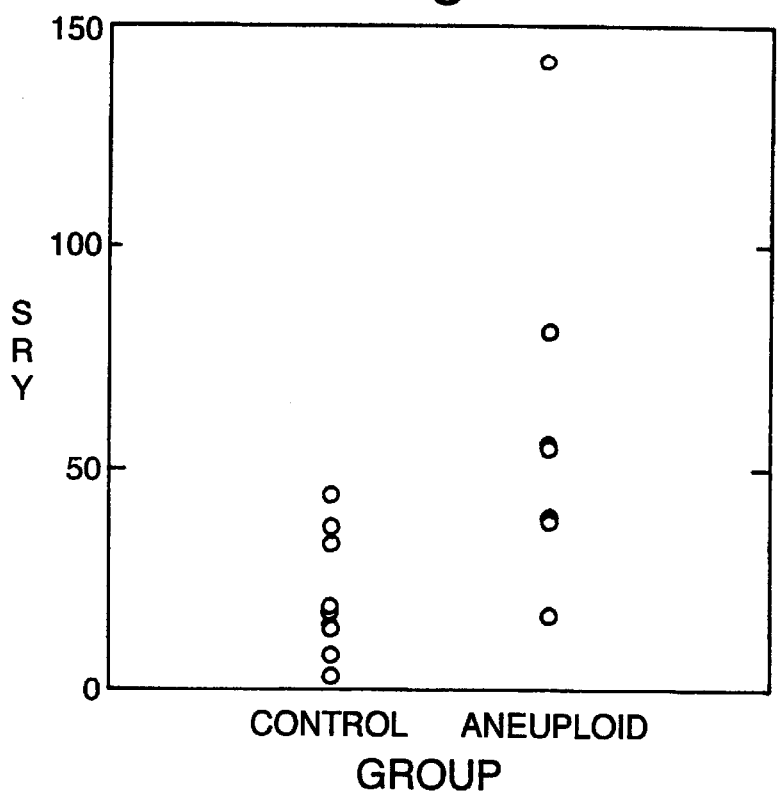
FIG. 1 shows increased foetal DNA in aneuploid pregnancies compared to control pregnancies.

The invention will now be illustrated in the following Examples, which do not in any way limit the scope of the invention.

EXAMPLES

Example 1

Analysis of foetal DNA for sex determination

Patients

Pregnant women attending the Nuffield Department of Obstetrics & Gynaecology, John Radcliffe Hospital, Oxford were recruited prior to amniocentesis or delivery. Ethics approval of the project was obtained from the Central Oxfordshire Research Ethics Committee. Informed consent was sought in each case. Five to ten ml of maternal peripheral blood was collected into an EDTA and a plain tube. For women undergoing amniocentesis, maternal blood was always collected prior to the procedure and 10 ml of amniotic fluid was also collected for foetal sex determination. For women recruited just prior to delivery, foetal sex was noted at the time of delivery. Control blood samples were also obtained from 10 non-pregnant female subjects and further sample processing was as for specimens obtained from pregnant individuals.

Sample preparation

Maternal blood samples were processed between 1 to 3 hours following venesection. Blood samples were centrifuged at 3000 g and plasma and serum were carefully removed from the EDTA-containing and plain tubes, respectively, and transferred into plain polypropylene tubes. Great care was taken to ensure that the buffy coat or the blood clot was undisturbed when plasma or serum samples, respectively, were removed. Following removal of the plasma samples, the red cell pellet and buffy coat were saved for DNA extraction using a Nucleon DNA extraction kit (Scotlabs, Strathclyde, Scotland, U.K.). The plasma and serum samples were then subjected to a second centrifugation at 3000 g and the recentrifuged plasma and serum samples were collected into fresh polypropylene tubes. The samples were stored at −20° C. until further processing.

DNA extraction from plasma and serum samples

Plasma and serum samples were processed for PCR using a modification of the method of Emanuel and Pestka (1993). In brief, 200 $\mu$l of plasma or serum was put into a 0.5 ml eppendorf tube. The sample was then heated at 99° C. for 5 minutes on a heat block. The heated sample was then centrifuged at maximum speed using a microcentrifuge. The clear supernatant was then collected and 10 $\mu$l was used for PCR.

DNA extraction from amniotic fluid

The amniotic fluid samples were processed for PCR using the method of Rebello et al (1991). One hundred $\mu$l of amniotic fluid was transferred into a 0.5 ml eppendorf tube and mixed with an equal volume of 10% Chelex-100 (Bio-Rad). Following the addition of 20 $\mu$l of mineral oil to prevent evaporation, the tube was incubated at 56° C. for 30 minutes on a heat block. Then, the tube was vortexed briefly and incubated at 99° C. for 20 minutes. The treated amniotic fluid was stored at 4° C. until PCR and 10 $\mu$l was used in a 100 $\mu$l reaction.

Polymerase chain reaction (PCR)

The polymerase chain reaction (PCR) was carried out essentially as described (Saiki et al 1988) using reagents obtained from a GeneAmp DNA Amplification Kit (Perkin Elmer, Foster City, Calif., USA). The detection of Y-specific foetal sequence from maternal plasma, serum and cellular DNA was carried out as described using primers Y1.7 and Y1.8, designed to amplify a single copy Y sequence (DYS14) (Lo et al 1990). The sequence of Y1.7 is 5' CAT CCA GAG CGT CCC TGG CTT 3' [SEQ ID NO: 1] and that of Y1.8 is 5° CTT TCC ACA GCC ACA TTT GTC 3' [SEQ ID NO: 2]. The Y-specific product was 198 bp. Sixty cycles of Hot Start PCR using Ampliwax technology were used on 10 $\mu$l of maternal plasma or serum or 100 ng of maternal nucleated blood cell DNA (denaturation step of 94° C. 1 minute and a combined reannealing/extension step of 57° C. 1 minute). Forty cycles were used for amplification of amniotic fluid. PCR products were analysed by agarose gel electrophoresis and ethidium bromide staining. PCR results were scored before the foetal sex was revealed to the investigator.

Results

Sensitivity of PCR assay

Serial dilutions of male genomic DNA in 1 $\mu$g of female genomic DNA were performed and amplified by the Y-PCR system using 60 cycles of amplification. Positive signals were detected up to the 100,000 dilution, i.e., approximately the equivalent of a single male cell.

Amplification of foetal DNA sequence from maternal plasma and serum

Maternal plasma and serum samples were collected from 43 pregnant women with gestational ages from 12 to 40 weeks. There were 30 male foetuses and 13 female foetuses. Of the 30 women bearing male foetuses, Y-positive signals were detected in 24 plasma samples and 21 serum samples, when 10 $\mu$l of the respective samples was used for PCR. When nucleated blood cell DNA was used for Y-PCR, positive signals were only detected in 5 of the 30 cases. None of the 13 women bearing female foetuses and none of the 10 non-pregnant female controls resulted in a positive Y signal when either plasma, serum or cellular DNA was amplified. Accuracy of this technique, even with serum/plasma samples of only 10 $\mu$l, is thus very high and most importantly it is high enough to be useful. It will be evident that accuracy can be improved to 100% or close to 100%, for example by using a larger volume of serum or plasma.

Example 2

Quantitative analysis of foetal DNA in maternal serum in aneuploid pregnancies

The prenatal screening and diagnosis of foetal chromosomal aneuploidies is an important part of modern obstetrical care. Due to the risks associated with invasive procedures such as amniocentesis and the impracticability of performing screening with invasive methods, much effort has been devoted to the development of non-invasive screening methods for foetal chromosomal aneuploidies. The two main non-invasive methods which have been developed are maternal serum biochemical screening and ultrasound examination for nuchal translucency. These methods are both associated with significant false-positive and false-negative rates.

The demonstration of foetal nucleated cells in maternal circulation offers a new source of foetal material for the non-invasive diagnosis of foetal chromosomal aneuploidies (Simpson et al 1993). By the use of foetal nucleated cell enrichment protocols, several groups have reported the detection of aneuploid foetal nucleated cells isolated from maternal blood (Elias et al 1992; Bianchi et al 1992). Recently, it has been demonstrated that there is increased foetal nucleated cell number in maternal circulation when the foetus is suffering from a chromosomal aneuploidy (Bianchi et al 1997).

Patients samples

Blood samples from pregnant women undergoing prenatal testing were collected prior to any invasive procedure. The foetal karyotype was confirmed by cytogenetic analysis of amniotic fluid or chorionic villus samples. Approval was obtained from the Research Ethics Committee of The Chinese University of Hong Kong. Blood samples were collected into plain tubes. Following blood clotting, the samples were centrifuged at 3000 g, and serum were carefully removed and transferred into plain polypropylene tubes. The samples were stored at −70° C. or −20° C. until further processing.

DNA extraction from plasma and serum samples

DNA from serum samples were extracted using a QIAamp Blood Kit (Qiagen, Hilden, Germany) using the "blood and body fluid protocol" as recommended by the manufacturer (Chen et al 1996). Four hundred to 800 $\mu$l of plasma/serum sample was used for DNA extraction per column. The exact amount used was documented to enable the calculation of target DNA concentration.

Real time quantitative PCR

Theoretical and practical aspects of real time quantitative PCR were previously described by Heid et al (1996). Real time quantitative PCR analysis was performed using a PE Applied Biosystems 7700 Sequence Detector (Foster City, Calif., U.S.A.) which is essentially a combined thermal cycler/fluorescence detector with the ability to monitor the progress of individual PCR reactions optically. The amplification and product reporting system used is based on the 5' nuclease assay (Holland et al 1991) (the TaqMan assay as marketed by Perkin-Elmer). In this system, apart from the two amplification primers as in conventional PCR, a dual labeled fluorogenic hybridisation probe is also included (Lee et al 1993; Livak et al 1995). One fluorescent dye serves as a reporter (FAM, i.e., 6-carboxyfluorescein) and its emission spectra is quenched by a second fluorescent dye (TAMRA, i.e., 6-carboxy-tetramethylrhodamine). During the extension phase of PCR, the 5' to 3'-exonuclease activity of the Taq DNA polymerase cleaves the reporter from the probe thus releasing it from the quencher, resulting in an increase in fluorescent emission at 518 nm. The PE Applied Biosystems 7700 Sequence Detector is able to measure the fluorescent spectra of the 96 amplification wells continuously during DNA amplification and the data are captured onto a Macintosh computer (Apple Computer, Cupertino, Calif., U.S.A.).

The SRY TaqMan system consisted of the amplification primers SRY-109F, 5'-TGG CGA TTA AGT CAA ATT CGC-3' [SEQ ID NO:3]; SRY-245R, 5'-CCC CCT AGT ACC CTG ACA ATG TAT T-3' [SEQ ID NO:4]; and a dual labeled fluorescent TaqMan probe SRY-142T, 5'-(FAM) AGC AGT AGA GCA GTC AGG GAG GCA GA(TAMRA)-3' [SEQ ID NO: 5]. Primer/probe combinations were designed using the Primer Express software (Perkin-Elmer, Foster City, Calif., U.S.A.). Sequence data for the SRY gene were obtained from the GenBank Sequence Database (accession number L08063).

TaqMan amplification reactions were set up in a reaction volume of 50 µl using components (except TaqMan probe and amplification primers) supplied in a TaqMan PCR Core Reagent Kit (Perkin-Elmer, Foster City, Calif., U.S.A.). The SRY TaqMan probe were custom-synthesised by PE Applied Biosystems. PCR primers were synthesised by Life Technologies (Gaithersburg, Md., U.S.A.). Each reaction contained 5 µl of 10× buffer A, 300 nM of each amplification primers, 100 nM of the SRY TaqMan probe, 4 mM $MgCl_2$, 200 µM each of dATP, dCTP and dGTP, 400 µM dUTP, 1.25 units of AmpliTaq Gold and 0.5 unit AmpErase uracil N-glycosylase. Five to ten µl of the extracted serum DNA was used for amplification. The exact amount used was recorded for subsequent concentration calculation. DNA amplifications were carried out in 96-well reaction plates that were frosted by the manufacturer to prevent light reflection and were closed using caps designed to prevent light scattering (Perkin-Elmer, Foster City, Calif., U.S.A.). Each sample was analysed in duplicate. A calibration curve was run in parallel and in duplicate with each analysis. The conversion factor of 6.6 pg of DNA per cell was used for expressing the results as copy numbers.

Thermal cycling was initiated with a 2-minute incubation at 50° C. for the uracil N-glycosylase to act, followed by a first denaturation step of 10 minutes at 95° C. Then, 40 cycles of 95° C. for 15 s and 60° C. for 1 minute were carried out.

Amplification data collected by the 7700 Sequence Detector and stored in the Macintosh computer were then analysed using the Sequence Detection System (SDS) software developed by PE Applied Biosystems. The mean quantity of each duplicate was used for further concentration calculation. The concentration expressed in copies/ml was calculated using the following equation:

$$C = Q \times V_{DNA}/V_{PCR} \times 1/V_{ext}$$

where

C=target concentration in plasma or serum (copies/ml);

Q=target quantity (copies) determined by sequence detector in a PCR;

$V_{DNA}$=total volume of DNA obtained following extraction, typically 50 µl per Qiagen extraction;

$V_{PCR}$=volume of DNA solution used for PCR, typically 5–10 µl $V_{ext}$=volume of plasma/serum extracted, typically 400–800 µl Anti-contamination measures Strict precautions against PCR contamination were used (Kwok et al 1989). Aerosol-resistant pipette tips were used for all liquid handling. Separate areas were used for the setting up of amplification reactions, the addition of DNA template and the carrying out of amplification reactions. The 7700 Sequence Detector offered an extra level of protection in that its optical detection system obviated the need to reopen the reaction tubes following the completion of the amplification reactions, thus minimising the possibility of carryover contamination. In addition, the TaqMan assay also included a further level of anti-contamination measure in the form of pre-amplification treatment using uracil N-glycosylase which destroyed uracil containing PCR products (Longo et al 1990). Multiple negative water blanks were included in every analysis.

Results

Development of real time quantitative PCR

To determine the dynamic range of real time quantitative PCR, serial dilutions of male DNA were made in water consisting of the DNA equivalent from 1,000 cells to 1 cell and subjected to analysis by the SRY TaqMan system. The fewer the number of target molecules, the more amplification cycles were needed to produce a certain quantity of reporter molecules. The system was sensitive enough to detect the DNA equivalent from a single target cell.

A parameter, termed the threshold cycle ($C_T$) could be defined which was set at 10 standard deviations above the mean base-line fluorescence calculated from cycles 1 to 15 and was proportional to the starting target copy number used for amplification (Heid et al 1996). A plot of the threshold cycle ($C_T$) against the input target quantity, with the latter plotted on a common log scale, demonstrated the large dynamic range and accuracy of real time quantitative PCR.

The real time quantitative SRY system was insensitive to the existence of background female DNA from 0 to 12,800 female genome-equivalents. This greatly simplified the application of this system as separate calibration curves did not have to be constructed for different cases due to the presence of different concentrations of foetal and maternal DNA.

Quantitative analysis of foetal SRY gene from maternal serum from aneuploid and control pregnancies Real time quantitative SRY PCR was carried out for serum DNA extracted from women bearing aneuploid and normal foetuses. Data from individual cases are plotted in FIG. 1. Foetal DNA concentration was higher in aneuploid than control pregnancies (Mann-Whitney U Test, p=0.006).

Discussion

In this study we demonstrate that the concentration of foetal DNA in maternal serum is elevated in aneuploid pregnancies. These results indicate that foetal DNA quantitation has the potential to be used as a new screening marker for foetal chromosomal aneuploidies. A large scale population-based study could be carried out to develop cutoff values for screening purposes. It would also be useful to investigate the correlation of foetal DNA concentration with the other biochemical markers for maternal serum biochemical screening.

The mechanism(s) by which increased amounts of foetal DNA is liberated into maternal circulation in aneuploid pregnancies require further research. One possibility is related to the increased numbers of foetal nucleated cells which are released into the maternal blood in aneuploid pregnancies (Bianchi et al 1997). Another possible mechanism may be increased cell death or turnover which may be associated with chromosomal aneuploidies.

Example 3

Non-invasive prenatal determination of foetal RhD status from plasma of RhD-negative pregnant women Introduction The rhesus blood group system is important in transfusion and clinical medicine, being involved in haemolytic disease of the newborn, transfusion reactions and autoimmune haemolytic anaemia. Despite the widespread use of rhesus immunoglobulin prophylaxis in rhesus D (RhD)-negative mothers, rhesus isoimmunisation still occurs. In those cases where the father is heterozygous for RhD gene, there is a 50% chance that the foetus is RhD-positive and 50% chance that the foetus is RhD-negative. The prenatal determination of foetal RhD status in these cases is clinically useful because no further prenatal invasive testing or therapeutic manoeuvres are necessary if the foetus can be shown to be RhD-negative.

Advances towards this goal have been made possible recently through the cloning of the human RhD gene (Le Van Kim et al 1992) and the demonstration that RhD-negative individuals lack the RhD gene (Colin et al 1991). Prenatal determination of foetal RhD status has been performed using PCR-based techniques on amniotic fluid samples (Bennett et al 1993).

A number of groups have also investigated the possibility of using foetal cells in maternal blood for the determination of foetal RhD status (Lo et al 1993). The main problem with this approach is that the system is not sufficiently reliable without foetal cell enrichment or isolation procedure as demonstrated by the high false-positive and false-negative rates on unenriched samples. Foetal cell enrichment or isolation procedures, on the other hand, are tedious and expensive to perform (Geifman-Holtzman et al 1996; Sekizawa et al 1996).

Our discovery of the presence of foetal DNA in maternal plasma and serum offers a new approach for non-invasive prenatal diagnosis.

Materials and Methods

Patients

Pregnant women attending the Nuffield Department of Obstetrics & Gynaecology were recruited with informed consent. Approval of the project was obtained from the Central Oxfordshire Research Ethics Committee. Women in the second trimester of pregnancy were recruited just prior to amniocentesis. Blood samples were collected prior to any invasive procedures. Ten ml of amniotic fluid was also collected for foetal RhD genotyping. Women in the third trimester of pregnancy were recruited just prior to delivery. A sample of cord blood was taken following delivery for the ascertainment of foetal RhD status by serological methods.

Sample preparation

Blood samples were collected into tubes containing EDTA. The samples were centrifuged at 3000 g, and plasma was carefully removed and transferred into plain polypropylene tubes. Great care was taken to ensure that the buffy coat was not disturbed. The buffy coat samples were stored at −20° C. until further processing. The plasma samples were then recentrifuged at 3000 g and plasma was again carefully removed and transferred into a fresh set of plain polypropylene tubes. The samples were stored at −20° C. until further processing.

DNA extraction from plasma and serum samples

DNA from plasma and buffy coat samples were extracted using a QIAamp Blood Kit (Qiagen, Hilden, Germany) using the "blood and body fluid protocol" as recommended by the manufacturer (Cher et al 1996). Eight hundred µl of plasma sample and 200 µl of buffy coat sample was used for DNA extraction per column.

Real time quantitative PCR

Real time quantitative PCR analysis was performed as described in Example 2 with the following modifications.

The RhD TaqMan system consisted of the amplification primers RD-A: 5'-CCT CTC ACT GTT GCC TGC ATT-3' [SEQ ID NO: 6]; RD-B: 5'-AGT GCC TGC GCG AAC ATT-3' [SEQ ID NO: 7]; and a dual labelled fluorescent TaqMan probe RD-T,5'-(FAM)TAC GTG AGA AAC GCT CAT GAC AGC AM GTC T(TAMRA)-3' [SEQ ID NO: 8]. Primer/probe combinations were designed using the Primer Express software (Perkin-Elmer, Foster City, Calif., U.S.A.). Sequence data for the RhD gene were as previously described (Le Van Kim et al 1992).

The beta-globin TaqMan system consisted of the amplification primers beta-globin-354F, 5'-GTG CAC CTG ACT CCT GAG GAG A-3' [SEQ ID NO: 9]; beta-globin-455R, 5'-CCT TGA TAC CM CCT GCC CAG-3'; and a dual labelled fluorescent TaqMan probe beta-globin-402T, 5'-(FAM)MG GTG AAC GTG GAT GM GTT GGT GG(TAMRA)-3' [SEQ ID NO: 10]. Primer/probe combinations were designed using the Primer Express software (Perkin-Elmer, Poster City, Calif., U.S.A.). Sequence data were obtained from the GenBank Sequence Database: accession number U01317.

Results

Development of real time TaqMan PCR

The real time sequence detector is able to measure the fluorescence intensity of the liberated reporter molecules cycle after cycle. A parameter, termed the threshold cycle ($C_T$), could be defined which was set at 10 standard deviations above the mean base-line fluorescence calculated from cycles 1 to 15 (Heid et al 1996). An amplification reaction in which the fluorescence intensity rises above the threshold during the course of thermal cycling is defined as a positive reaction.

To determine the sensitivity of TaqMan PCR, serial dilutions of genomic DNA isolated from a RhD-positive individual were made in water consisting of the DNA equivalent from 1,000 cells to 1 cell and subjected to analysis by the SRY TaqMan system. The fewer the number of target molecules, the more amplification cycles were needed to produce a certain quantity of reporter molecules. The system was sensitive enough to detect the DNA equivalent from a single target cell.

Correlation of serology and genotyping of the RhD-negative women

The 21 pregnant women enrolled in this study were all serologically RhD-negative. Genomic DNA (10 ng) isolated from the buffy coat from each woman was subjected to the RhD TaqMan assay and in each case a negative result was found; thus demonstrating complete correlation between the serology and genotyping.

RhD genotyping from DNA isolated from maternal plasma

DNA extracted from the plasma of the 21 RhD-negative pregnant women were subjected to the RhD TaqMan assay. There was complete correlation between the foetal RhD genotype predicted from maternal plasma analysis and the result obtained from genotyping the amniotic fluid and serological testing of the cord blood (Table 1).

As a control for the amplifiability of DNA extracted from maternal plasma, these samples were also subjected to the beta-globin TaqMan assay. In every case, a positive TaqMan signal was generated.

Discussion

In this study we have demonstrated the feasibility of performing non-invasive foetal RhD genotyping from maternal plasma. This represents the first description of single gene diagnosis from maternal plasma. Our results indicate that this form of genotyping is highly accurate and can potentially be used for clinical diagnosis. This high accuracy is probably the result of the high concentration of foetal DNA in maternal plasma.

The rhesus family of polypeptides are encoded by two related genes: the CcEe gene and the RhD gene (Le Van Kim et a/ 1992; Chérif-Zahar et al 1990). Due to the complexity of the Rh genetic systems, a number of primer sets have been described for RhD genotyping (Bennet et al 1993; Lo et al 1993; Aubin et al 1997). In order to ensure the accuracy of our genotyping system in the study samples, we performed a control genotyping of buffy coat DNA of our patient population. In all cases there was complete correlation between serology and genotype. It is likely that for robust clinical diagnosis, multiple primer sets are preferred. The TaqMan chemistry can easily accommodate the inclusion of multiple primer/probe sets.

The correlation between the severity of foetal haemolytic disease and maternal and-D level is an area which required further investigation. It is possible that increased amount of foetal DNA is liberated into the maternal circulation in the presence of increased foetal haemolysis.

TABLE 1

RhDd genotyping from plasma from RhD-negative pregnant women

| Case | Foetal RhD genotype | Maternal Plasma RhD TaqMan signal |
|---|---|---|
| 1 | − | − |
| 2 | − | − |
| 3 | − | − |
| 4 | + | + |
| 5 | + | + |
| 6 | − | − |
| 7 | − | − |
| 8 | + | + |
| 9 | + | + |
| 10 | − | − |
| 11 | + | + |
| 12 | + | + |
| 13 | + | + |
| 14 | + | + |
| 15 | − | − |
| 16 | + | + |
| 17 | + | + |
| 18 | + | + |
| 19 | + | + |
| 20 | + | + |
| 21 | + | + |

Example 4

Elevation of foetal DNA concentration in maternal serum in pre-eclamptic pregnancies Introduction Pre-eclampsia is an important cause of maternal and foetal mortality and morbidity. Despite much research, the pathogenesis of this condition is still unclear. The disorder is mainly recognised by the concurrence of pregnancy-induced changes which regress after delivery, of which hypertension and proteinuria are the most commonly used clinical criteria. Some investigators have suggested that pre-eclampsia is the result of abnormal trophoblastic implantation, probably mediated by immunological mechanisms. Other investigators have found pathological changes in the spiral arteries in the decidua and myometrium in which partial occlusion by fibrinoid material is one feature.

In this Example we use a real time quantitative PCR assay to show the concentration of foetal DNA in the serum of women suffering from pre-eclampsia. Y chromosomal sequences from male foetuses were used as a foetal marker.

Materials and Methods

Patients

Pregnant women attending the Department of Obstetrics & Gynaecology at the Prince of Wales Hospital, Shatin, Hong Kong and the Nuffield Department of Obstetrics & Gynaecology, Oxford, U.K. were recruited with informed consent. Approval was obtained from the Research Ethics Committee of The Chinese University of Hong Kong and the Central Oxfordshire Research Ethics Committee. Pre-eclampsia was defined as a sustained rise in diastolic blood pressure to 90 mmHg or higher from previously lower values, with new and sustained proteinuria in the absence of urinary tract infection. The control pregnant women were not on medication and had no hypertension or proteinuria (defined as more than a trace on dipstick urinalysis). The pre-eclamptic and control subjects were matched for gestational age.

Sample preparation

Blood samples were collected into plain tubes. Following blood clotting, the samples were centrifuged at 3000 g, and serum were carefully removed and transferred into plain polypropylene tubes. The samples were stored at −70° C. or −20° C. until further processing.

DNA extraction from plasma and serum samples DNA from serum samples were extracted using a QIAamp Blood Kit (Qiagen, Hilden, Germany) using the "blood and body fluid protocol" as recommended by the manufacturer (Chen et al 1996). Four hundred to 800 $\mu$l of plasma/serum sample was used for DNA extraction per column. The exact amount used was documented to enable the calculation of target DNA concentration.

Real time quantitative PCR

Real time quantitative PCR analysis was performed as described in Example 2.

Results

Quantitative analysis of foetal SRYgene from maternal serum

Real time quantitative SRY PCR was carried out for serum DNA extracted from pre-eclamptic and control patients. Data from individual cases are plotted in FIG. 2. The median foetal DNA concentrations in pre-eclamptic and control pregnancies were 381 copies/ml and 76 copies/ml, respectively. Foetal DNA concentration was higher in pre-eclamptic than control pregnancies (Mann-Whitney U Test, p<0.0001).

Discussion

Our data indicate that the concentration of foetal DNA is higher in pre-eclamptic compared with non-pre-eclamptic pregnancies. These results indicate that foetal DNA concentration measurement in maternal plasma may be used as a new marker for pre-eclampsia. Compared with other markers for pre-eclampsia, foetal DNA measurement is unique in that it is a genetic marker while other markers, such as activin A and inhibin A, are generally hormonal markers. By its nature, a test based on a genetic marker has the advantage that it is completely foetal-specific.

Further research will be required to investigate whether the level of foetal DNA is related to the severity of pre-eclampsia. Our discovery also opens up research into the potential application of foetal DNA quantitation to predict the occurrence of pre-eclampsia, prior to the development of clinical signs such as hypertension and proteinuria.

The mechanism by which increased amounts of foetal DNA is liberated into the circulation of pre-eclamptic women is unclear at present. Possible mechanisms include damage to the placental interface resulting in foetal cell death and the consequent release of foetal DNA into maternal circulation. A second mechanism is due to the increased trafficking of foetal cells into maternal circulation in pre-eclampsia. Foetal DNA is then liberated following their destruction in the maternal circulation. Future studies correlating the levels of foetal cells and foetal DNA would be necessary to address these issues.

Example 5

Quantitative analysis of foetal DNA in maternal plasma and serum

Introduction

We have demonstrated that foetal DNA is present in maternal plasma and serum. Detection of foetal DNA sequences was possible in 80% and 70% of cases using just 10 μl of boiled plasma and serum, respectively (Lo et al. 1997).

These observations indicate that maternal plasma/serum DNA may be a useful source of material for the non-invasive prenatal diagnosis of certain genetic disorders. To demonstrate that clinical applications are possible, a number of important questions need to be answered. First, foetal DNA in maternal plasma and serum needs to be shown to be present in sufficient quantities for reliable molecular diagnosis to be carried out. Second, data on the variation of foetal DNA in maternal plasma and serum with regard to gestation age is required to determine the applicability of this technology to early prenatal diagnosis.

In this Example we have addressed both of these issues by developing a real time quantitative TaqMan polymerase chain reaction (PCR) assay (Heid et al. 1996) for measuring the copy numbers of foetal DNA molecules in maternal plasma and serum. This technique permits continuous optical monitoring of the progress of an amplification reaction, giving accurate target quantitation over a wide concentration range. Our data show that foetal DNA is present in maternal plasma and serum at concentrations similar to those achieved by many foetal cell enrichment protocols. We have also investigated the changes of foetal DNA concentration in maternal serum at different gestational ages. Using this plasma or serum-based approach, we show that the reliable detection of foetal DNA is achievable and therefore useful for the non-invasive prenatal diagnosis of selected genetic disorders.

Subjects and Methods

Patients

Pregnant women attending the Department of Obstetrics & Gynecology at the Prince of Wales Hospital, Shatin, Hong Kong were recruited with informed consent. Approval was obtained from the Research Ethics Committee of The Chinese University of Hong Kong. For women studied at a single time point, early pregnancy samples were obtained prior to amniocentesis or chorionic villus sampling while late pregnancy samples were collected just prior to delivery. Five to ten ml of maternal peripheral blood was collected each into one tube containing EDTA and one plain tube. Subjects studied at multiple time points were recruited from the in vitro fertilization program, prior to conception. Five to ten ml of maternal blood from these subjects was collected into a plain tube at each studied time point. For women undergoing prenatal diagnosis, the sex of the baby was ascertained from cytogenetic results from the amniocentesis or chorionic villus samples. For women recruited just prior to delivery or from the in vitro fertilization program, foetal sex was noted at the time of delivery.

Sample preparation

Blood samples were centrifuged at 3000 g, and plasma and serum were carefully removed from the EDTA-containing and plain tubes, respectively, and transferred into plain polypropylene tubes. Great care was taken to ensure that the buffy coat or the blood clot was undisturbed when plasma or serum samples, respectively, were removed. The plasma and serum samples were recentrifuged at 3000 g and the supernatants were collected into fresh polypropylene tubes. The samples were stored at −20° C. until further processing.

DNA extraction from plasma and serum samples DNA from plasma and serum samples were extracted using a QIAamp Blood Kit (Qiagen, Hilden, Germany) using the "blood and body fluid protocol" as recommended by the manufacturer (Chen et al. 1996). Four hundred to 800 l of plasma/serum sample was used for DNA extraction per column. The exact amount used was documented to enable the calculation of target DNA concentration.

Real time quantitative PCR

Real time quantitative PCR analysis was performed as described in Example 2, using the SRY TaqMan system and the beta-globin TaqMan system described in the previous Examples.

Identical thermal profile was used for both the SRY and beta-globin TaqMan systems. Thermal cycling was initiated with a 2-minute incubation at 50° C. for the uracil N-glycosylase to act, followed by a first denaturation step of 10 minutes at 95° C. Then, 40 cycles of 95° C. for 15 s and 60° C. for 1 minute were carried out.

Results

Development of real time quantitative PCR

Figure 3A:
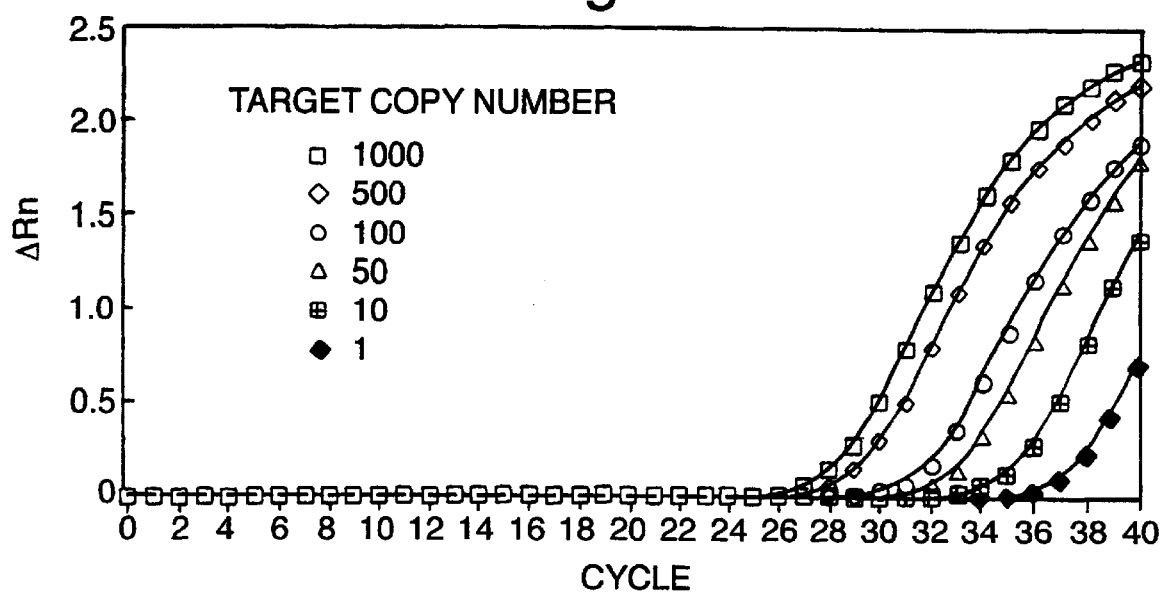
FIGS. 3A and 3B show an amplification curve and threshold cycle for real time quantitative PCR.

To determine the dynamic range of real time quantitative PCR, serial dilutions of male DNA were made in water consisting of the DNA equivalent from 1,000 cells to 1 cell and subjected to analysis by the SRY TaqMan system. FIG. 3A demonstrates that the amplification curve shifted to the right as the input target quantity was reduced. This was expected as reactions with fewer target molecules required more amplification cycles to produce a certain quantity of reporter molecules than reactions with more target molecules. The system was sensitive enough to detect the DNA equivalent from a single target cell.

Figure 3B:
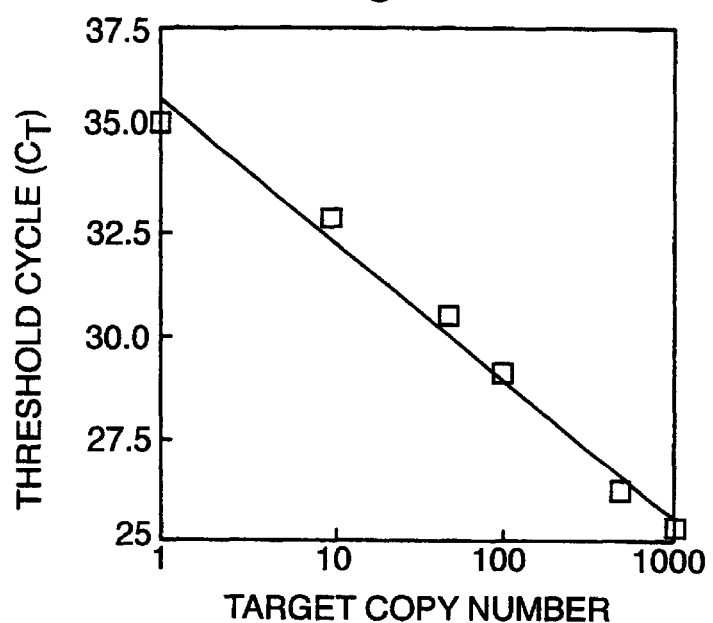
Figure 4A:
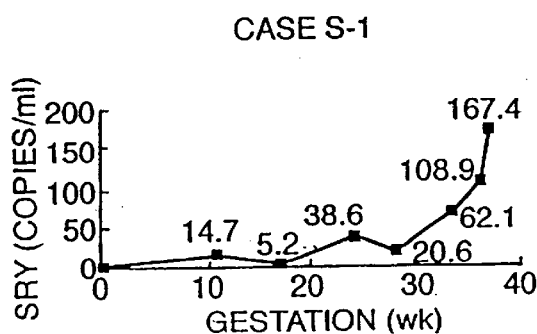
FIGS. 4a–4l show foetal DNA concentrations in maternal samples for a number of subjects at different stages of gestation.
Figure 4B:
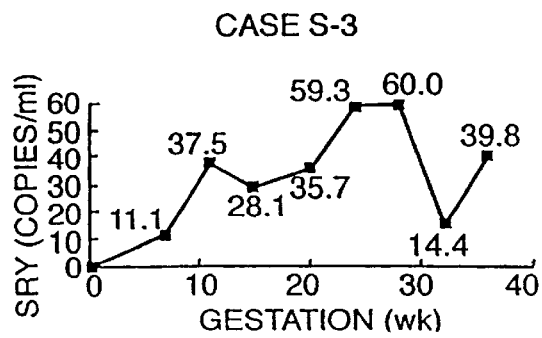
Figure 4C:
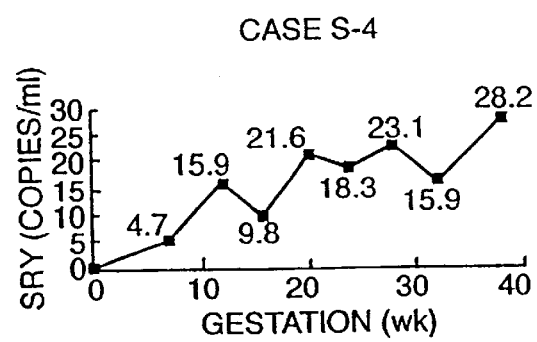
Figure 4D:
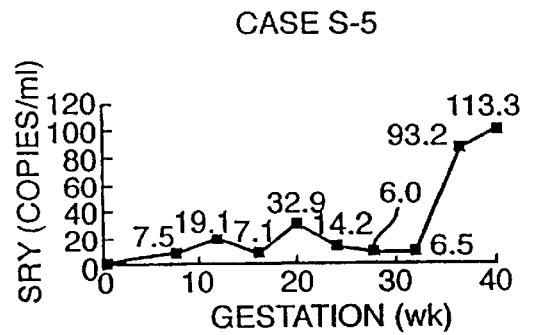
Figure 4E:
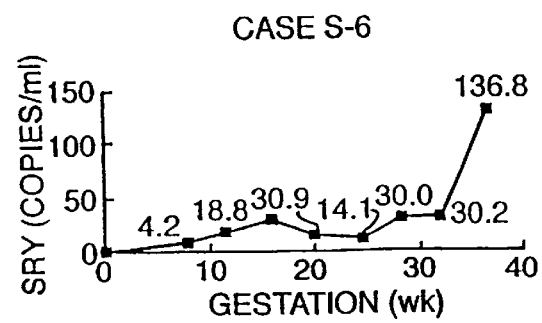
Figure 4F:
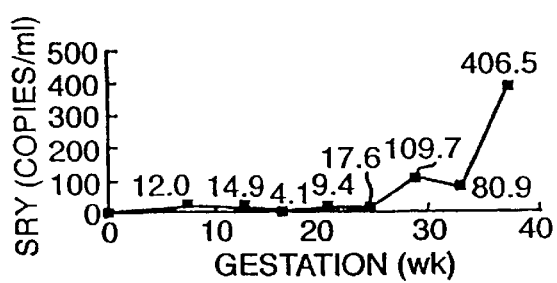
Figures 4G, 4H:
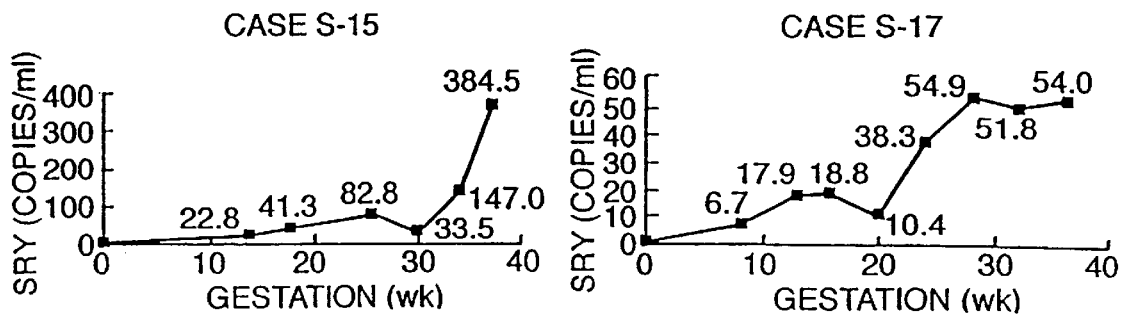
Figures 4I, 4J:
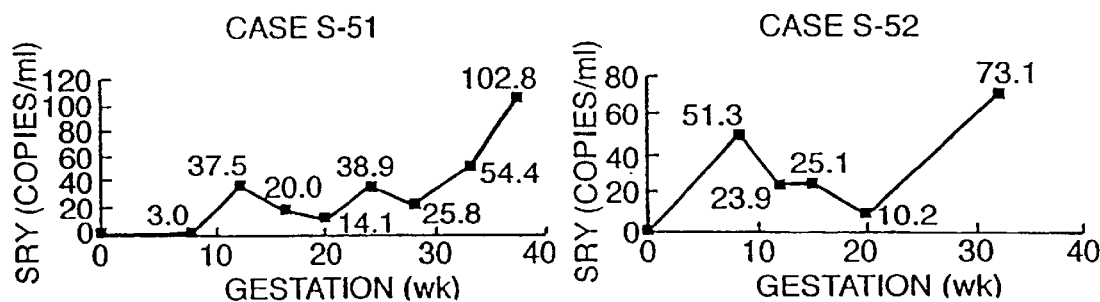
Figures 4K, 4L:
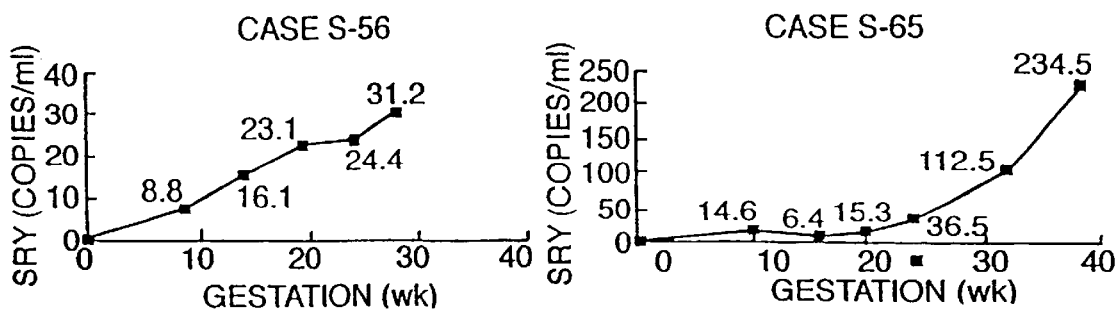

FIG. 3B shows a plot of the threshold cycle ($C_T$) against the input target quantity, with the latter plotted on a common log scale. The $C_T$ was set at 10 standard deviations above the mean base-line fluorescence calculated from cycles 1 to 15 and was proportional to the starting target copy number used for amplification (Heid et al. 1996). The linearity of the graph demonstrates the large dynamic range and accuracy of real time quantitative PCR. Similar results were obtained using the beta-globin TaqMan system (results not shown).

The real time quantitative SRY system was insensitive to the existence of background female DNA from 0 to 12,800 female genome-equivalents. This greatly simplified the application of this system as within this range, separate calibration curves did not have to be constructed for different cases due to the presence of different concentrations of foetal and maternal DNA.

The reproducibility of DNA extraction from plasma and serum using the Qiagen protocol was tested by performing replicate extractions (10 for each case) from plasma and serum samples from normal individuals. These replicate extractions were then subjected to real time quantitative PCR using the beta-globin system. The coefficient of variation (CV) of $C_T$ values of these replicate extractions was 1.1%.

Quantitative analysis using the real time beta-globin TaqMan system

The concentration of beta-globin sequences in maternal plasma and serum samples was used as a measure of the total amount of extracted DNA, i.e., maternal and foetal DNA extracted from plasma and serum samples from 50 pregnant women was analysed using the beta-globin TaqMan system. Twenty-five cases were recruited during the first and second trimesters (gestational age: 11 to 17 weeks) and were denoted as early pregnancy samples in Table 2. The other twenty-five cases were recruited just prior to delivery (gestational age: 37 to 43 weeks) and were denoted as late pregnancy samples in Table 1. The concentrations of beta-globin sequences in maternal plasma and serum are listed in Table 2. These results show that serum contains more DNA than plasma (Wilcoxon Signed Rank Test, p<0.0005), with a mean concentration of serum DNA 14.6 times that of plasma DNA in our studied population. The concentration of beta-globin sequences in maternal plasma from early and late pregnancy samples are compared in Table 2. These data show that the total amount of plasma DNA increases as pregnancy progresses (Mann-Whitney Rank Sum Test, p<0.0005).

Quantitative analysis of foetal SRY gene from maternal plasma and serum

Real time quantitative analysis using the SRY TaqMan system was carried out on DNA extracted from maternal plasma and serum to determine the amount of foetal DNA. Of the 25 early pregnancy samples (gestational age: 11 to 17 weeks), 13 were from women bearing male foetuses and 12 were from women bearing female foetuses. Of the 25 late pregnancy samples (gestational age: 37 to 43 weeks), 14 were from women bearing male foetuses and 11 were from women bearing female foetuses. A positive signal was obtained in each of the 27 women bearing male foetuses and no signal was detected in each of the 23 women bearing female foetuses. Fourteen women had a history of delivering a previous male baby and 5 of these were carrying a female baby in the current studied pregnancy.

Quantitative SRY data from the 27 women bearing male foetuses are summarised in Table 3. These data show that the concentrations of foetal DNA in plasma and serum are higher in late gestation than in early gestation (Mann-Whitney Rank Sum Test, p<0.0005). The mean concentrations of foetal DNA in maternal plasma and serum are 11.5 times and 11.9 times, respectively, higher in late gestation compared with early gestation. The absolute concentrations of foetal DNA in maternal plasma and serum were similar in individual cases. The fractional concentration of foetal DNA in early pregnancy ranges from 0.39% to 11.9% (mean: 3.4%) in plasma and 0.014% to 0.54% (mean: 0.13%) in serum. In late pregnancy, the fraction of foetal DNA ranges from 2.33% to 11.4% (mean: 6.2%) in plasma and 0.032% to 3.97% (mean: 1.0%) in serum.

Sequential follow up of women who conceived by in vitro fertilization

Twenty women who conceived by in vitro fertilization (IVF) were followed up at pre-conception and at multiple time points during pregnancy. All twenty subjects had singleton pregnancies as determined by ultrasound scanning. Twelve women delivered male babies and the remaining 8 delivered female babies. None of the women carrying male foetuses had a history of pregnancy-associated complications. Subject S-51 (FIG. 4) underwent chorionic villus sampling at 12 weeks. Subjects S-1 and S-56 (FIG. 4) had amniocentesis at 16 and 17 weeks, respectively. A total of 163 serum samples from these 20 women were analysed using the real time quantitative SRY TaqMan system. None of the 65 serum samples from the 8 women bearing female babies gave a positive SRY signal. The concentrations of foetal DNA in the 98 serum samples from women carrying male babies are plotted in FIGS. 4a–4l.

Discussion

We have developed an accurate real time quantitative PCR system for determining the concentration of foetal DNA in maternal plasma and serum. This system has a number of advantages: (1) a large dynamic range of over 5 orders of magnitude (Heid et al. 1996); (2) a high throughput and fast turnaround time—96 samples could be simultaneously amplified and quantified in approximately 2 hours; and (3) the use of a homogeneous amplification/detection system which requires no post-PCR processing and therefore minimizes the risk of carryover contamination.

The most important observation in this study is the very high concentration of foetal DNA in maternal plasma and serum. Bianchi et al reported that the average number of foetal cells in maternal blood in normal pregnancies was 19 in 16 ml of maternal blood, i.e., 1.2 cells/ml during the second trimester (Bianchi et al. 1997). Therefore, the mean concentration of foetal DNA in maternal plasma and serum is 21.2 (25.4/1.2) and 23.9 (28.7/1.2) times, respectively, higher than that in the cellular fraction of maternal blood at the same gestation. The relative concentration of foetal to total plasma DNA is even higher. Thus, in early pregnancy, foetal DNA in maternal plasma constitutes a mean of 3.4% of the total plasma DNA. The respective figure in late pregnancy is 6.2%. Hamada et al reported that the frequency of foetal cells in the second trimester was 0.0035% while that in the third trimester was 0.008% (Hamada et a/. 1993). The fetomaternal ratio is, therefore, 97Sfold and 775-fold higher in maternal plasma than in the cellular fraction at the respective gestational age. Indeed, the fetomaternal ratio in plasma DNA is comparable to that following many foetal cell enrichment protocols. For example, Bianchi et al reported that following foetal nucleated red cell enrichment using fluorescence activated cell sorting, the resulting foetal cells constituted 0.001%–5% of the sorted cell populations as determined by quantitative PCR analysis (Bianchi et al. 1994). In a similar study using cell sorting and foetal cell detection using fluorescence in situ hybridization, Sohda et al found that on average 4.6% of the sorted cells were of foetal origin (Sohda et al. 1997). Maternal plasma, therefore, offers an easily accessible foetal DNA source for prenatal genetic analysis.

We have demonstrated that the absolute concentration of foetal DNA in maternal plasma is similar to that in maternal serum. The main difference lies in the presence of a larger quantity of background maternal DNA in serum compared with plasma, possibly due to the liberation of DNA during the clotting process. While this exerts no noticeable effect on the efficiency of foetal DNA detection using the real time TaqMan system, it is possible that with the use of less sensitive methods, e.g., conventional PCR followed by ethidium stained agarose gel electrophoresis, maternal plasma may be preferable to maternal serum for robust foetal DNA detection.

The high concentration of foetal DNA in maternal plasma and serum has allowed us to reliably detect the presence of foetal genetic material. Of the 263 serum or plasma samples analysed in this study, we were able to detect foetal SRY gene in maternal plasma or serum from every subject who was carrying a male baby at the time of venesection. This robust detection rate was obtained using DNA extracted from just 40–80 $\mu$l of maternal plasma and serum. This volume represents a 4–8 fold increase over the 10 $\mu$l of boiled maternal plasma or serum reported in our previous study (Lo et al. 1997) and results in significant improvement in sensitivity. The specificity was preserved as we did not observe amplification signals from samples obtained pre-conception or from subjects carrying a female foetus. From the data obtained thus far, plasma/serum analysis did not appear to be significantly affected by the persistence of foetal cells from previous pregnancies (Bianchi et al. 1996). Thus, we did not obtain any false positive results from women who had carried a previous male baby but who were carrying a female baby at the time of blood sampling for this study.

The sequential study on patients undergoing IVF gave a number of important results. First, all of the 12 patients carrying male babies were shown to be negative for SRY sequences in their sera prior to conception. This provided convincing evidence that the SRY sequence detected by the TaqMan assay did indeed originate from the male foetus in the current pregnancy. Second, we were able to detect foetal SRY sequences as early as the 7th week of gestation; thus indicating that foetal genetic analysis in maternal plasma/serum could be used in the first trimester. Third, we showed that foetal DNA concentration increased as pregnancy progressed (FIGS. 4a–4l). This last point was also confirmed by data obtained from women studied at a single time point. Women recruited late in pregnancy had higher foetal DNA concentrations in their plasma and serum (Table 3).

In addition to the increase in foetal DNA concentration as pregnancy progresses, our data also indicate that maternal plasma DNA also increases with gestation (Table 2). The biologic basis for this phenomenon is unclear at present. Possible explanations include the increase in size of the fetomaternal interface as gestation progresses and possible reduction in DNA clearance associated with other physiologic changes in pregnancy.

For selected disorders, foetal genetic information could be acquired more economically and rapidly from maternal plasma or serum than by using foetal cells isolated from maternal blood. We envisage that foetal DNA analysis in maternal plasma and serum would be most useful in situations where the determination of foetal-derived paternally-inherited polymorphisms/mutations or genes would be helpful in clinical prenatal diagnosis (Lo et al. 1994). Examples include foetal sex determination for the prenatal diagnosis of sex-linked disorders, foetal rhesus D status determination in sensitized rhesus negative pregnant women (Lo et al. 1993), autosomal dominant disorders in which the father carries the mutation and autosomal recessive genetic disorders in which the father and mother carry different mutations (Lo et al. 1994), e.g., certain hemoglobinopathies (Camaschella et al. 1990) and cystic fibrosis. Due to the much reduced maternal background and high foetal DNA concentration in maternal plasma and serum, we predict that this type of analysis would be much more robust compared with their application for detecting unsorted foetal cells in maternal blood. The ability for allelic discrimination (Lee et al. 1993; Livak et al. 1995) allows the homogeneous TaqMan assay to be used for this purpose. The high throughput and anti-contamination capability of this system makes it an attractive candidate for large scale clinical application.

Bianchi et al recently reported that foetal cells in maternal blood were increased in aneuploid pregnancies (Bianchi et al. 1997) and it has been demonstrated (Example 2) that the foetal DNA concentration in maternal plasma and serum is also elevated in these pregnancies. This provides a new screening test for foetal chromosomal disorders. For this application, foetal DNA quantitation systems can be developed for polymorphic markers outside the Y chromosome so that quantitation can be applied to female foetuses. Autosomal polymorphic systems which may be used for this purpose have already been described (Lo et al. 1996).

However, foetal cell isolation techniques would still be necessary for a definitive cytogenetic diagnosis. Similarly, foetal cell isolation would also be required for direct mutational analysis of autosomal recessive disorders caused by a single mutation. It is likely that foetal cell isolation and analysis of foetal DNA in maternal plasma/serum would be used as complementary techniques for non-invasive prenatal diagnosis.

The biologic basis by which foetal DNA is liberated into maternal plasma remains to be elucidated. It is possible that foetal DNA is released from cell lysis resulting from physical and immunologic damage, or through developmentally associated apoptosis of foetal tissues. It is also likely that increased amounts of foetal DNA may be found in conditions associated with placental damage, such as pre-eclampsia. The real time quantitative PCR system described here offers a powerful tool to study these unexplored pathophysiologic aspects of foetal DNA in maternal plasma and may improve our understanding of the fetomaternal relationship.

TABLE 2

Quantitative analysis of maternal plasma and serum using the beta-globin TaqMan assay

|  | Mean (copies/ml) | Median (copies/ml) | Range (copies/ml) |
| --- | --- | --- | --- |
| Plasma (Early + Late Pregnancy) | 3466 | 1594 | 356–31875 |
| Serum (Early + Late Pregnancy) | 50651 | 34688 | 5813–243750 |
| Plasma (Early Pregnancy) | 986 | 975 | 356–1856 |
| Plasma (Late Pregnancy) | 5945 | 4313 | 1125–31875 |

TABLE 3

Quantitation of foetal DNA in maternal plasma and serum: relationship with gestational age

| | SRY concentration (copies/ml) | | | |
| --- | --- | --- | --- | --- |
| | Early Pregnancy | | Late Pregnancy | |
| | Plasma | Serum | Plasma | Serum |
| Range | 3.3–69.4 | 4.0–58.1 | 76.9–769 | 33.8–900 |
| Mean | 25.4 | 28.7 | 292.2 | 342.1 |
| Median | 20.6 | 19.5 | 244.0 | 286.0 |

Figure Legends

FIG. 1. Foetal DNA in maternal serum from women carrying aneuploid and normal foetuses. The control and aneuploid groups are as indicated on the x-axis. The foetal SRY DNA concentrations expressed in copies/ml are plotted on the y-axis.

Figure 2:
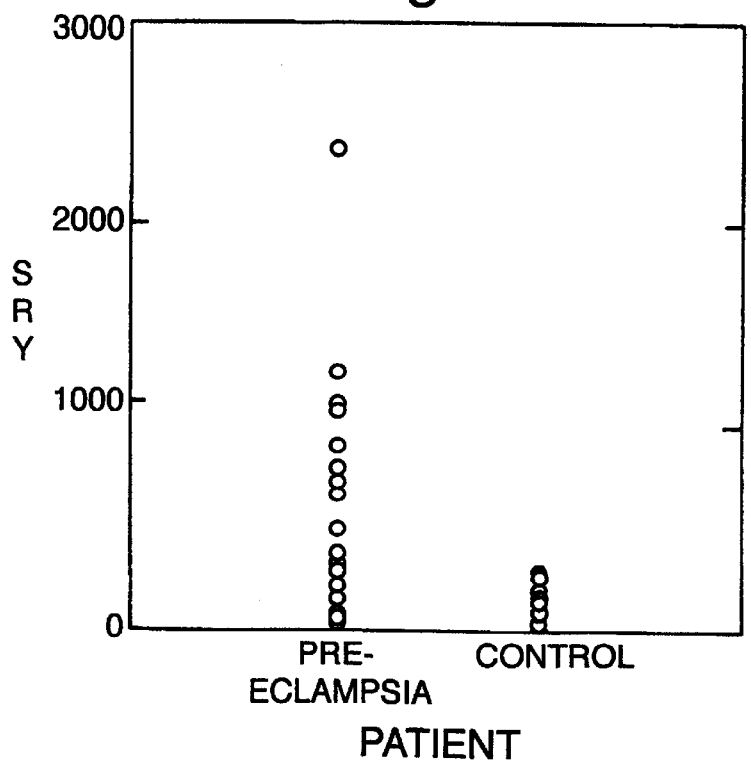
FIG. 2 shows increased foetal DNA in pre-eclampsia compared to control pregnancies.

FIG. 2. Foetal DNA in maternal serum in pre-eclamptic and non-pre-eclamptic pregnancies. The pre-eclamptic and control groups are as indicated on the x-axis. The foetal SRY DNA concentrations expressed in copies/ml are plotted on the y-axis.

FIGS. 3A and 3B. Real time quantitative PCR. A, Amplification plots obtained using real time quantitative PCR for the SRY gene. Each plot corresponds to a particular input target quantity marked by a corresponding symbol. The x-axis denotes the cycle number of a quantitative PCR reaction. The y-axis denotes the $\Delta Rn$ which is the fluorescence intensity over the background (Heid et al. 1996). B, Plot of the threshold cycle ($C_T$) against the input target quantity (common log scale). The correlation coefficient is 0.986.

FIGS. 4a–4l. Sequential study of 12 women bearing male fetuses who conceived by in vitro fertilization. Each case is denoted by a unique recruitment case number. The x-axis denotes the gestation at which the serum sample was obtained. A gestation age of zero denotes the pre-conception sample. The y-axis denotes the concentration of foetal SRY in maternal serum expressed in copies/ml. The scale has been optimized for the concentration range for each case.

References

Aubin J T, Le Van Kim C, Mouro I, et al. Specificity and sensitivity of RhD genotyping methods by PCR-based DNA amplification. Br J Haematol 1997; 98:356–364.

Bennett P R, Le Van Kim C, Colin Y, et al. Prenatal determination of foetal RhD type by DNA amplification. N Engl J Med 1993; 329:607–610.

Bianchi D W, Mahr A, Zickwolf G K, Houseal T W, Flint A F, Klinger K W. Detection of foetal cells with 47,XY,+21 karyotype in maternal peripheral blood. Hum Genet 1992; 90:368–370.

Bianchi D W, Shuber A P, DeMaria M A, Fougner A C, Klinger K W (1994) Foetal cells in maternal blood: determination of purity and yield by quantitative PCR. Am J Obstet Gynecol 171:922–926

Bianchi D W, Williams J M, Pelletier C, Klinger K W, Shuber A P. Foetal cell quantitation in maternal blood samples from normal and aneuploid pregnancies. Pediatr Res 1996; 39:142A.

Bianchi D W, Williams J M, Sullivan L M, Hanson F W, Klinger K W, Shuber A P. PCR quantitation of foetal cells in maternal blood in normal and aneuploid pregnancies. Am J Hum Genet 1997; 61:822–829.

Camaschella C, Alfarano A, Gottardi E, et al. Prenatal diagnosis of foetal hemoglobin Lepore-Boston disease on maternal peripheral blood. Blood 1990; 75:2102–106.

Chérif-Zahar B, Bloy C, Le Van Kim C, et al. Molecular cloning and protein structure of a human blood group Rh polypeptide. Proc Natl Acad Sci U S A 1990; 87:6243–6247.

Chen X Q, Stroun M, Magnenat J- L, et al. Microsatellite alterations in plasma DNA of small cell lung cancer patients. Nat Med 1996; 2:1033–35.

Cheung M C, Goldberg J D, Kan Y W. Prenatal diagnosis of sickle cell anemia and thalassemia by analysis of foetal cells in maternal blood. Nat Genet 1996; 14:264–68.

Colin Y, Cherif-Zahar B, Le Van Kim C, Raynal V, van Huffel V, Cartron J- P. Genetic basis of the RhD-positive and RhD-negative blood group polymorphism as determined by Southern analysis. Blood 1991; 78:2747–2752.

Elias S, Price J, Dockter M, Wachtel S, Tharapel A, Simpson J L. First trimester prenatal diagnosis of trisomy 21 in foetal cells from maternal blood. Lancet 1992; 340:1033.

Emanuel S L, Pestka S. Amplification of specific gene products from human serum. GATA 1993; 10:144–46.

Frickhofen N. & Young N. S. A rapid method of sample preparation for detection of DNA viruses in human serum by polymerase chain reaction. J.Virological Methods 1991; 35:65–72.

Geifman-Holtzman O, Bernstein I M, Berry S M, et al. Petal RhD genotyping in foetal cells flow-sorted from maternal blood. Am. J. Obstet. Gynecol. 1996; 174:818–822.

Hamada H, Arinami T, Kubo T, Hamaguchi H, Iwasaki H (1993) Foetal nucleated cells in maternal peripheral blood: frequency and relationship to gestational age. Hum Genet 91:427432

Held C. A., Stevens J., Livak K. J., Williams P. M. Real time quantitative PCR. Genome Research 1996; 6:986–994.

Holland P M, Abramson R D, Watson R, Gelfand D H. Detection of specific polymerase chain reaction product by utilising the 5'-3' exonuclease activity of the *Thermus aquaticus* DNA polymerase. Proc Natl Acad Sci USA 1991; 88:7276–7280.

Kwok S, Higuchi R. Avoiding false positives with PCR. Nature 1989; 339:237–238.

Le Van Kim C, Mouro I, Cherif-Zahar B, et al. Molecular cloning and primary structure of the human blood group RhD polypeptide. Proc Natl Acad Sci USA 1992; 89:10925–10929.

Lee L G, Connell C R, Bloch W. Alldic discrimination by nick-translation PCR with fluorogenic probes. Nucleic Acids Res 1993; 21:3761–3766.

Livak K J, Flood S J, Marmaro J, Giusti W, Deetz K. Oligonucleotides with fluorescent dyes at opposite ends provide a quenched probe system useful for detecting PCR product and nucleic acid hybridization. PCR Methods Appl 1995; 4:357–362.

Lo Y M D, Corbetta N, Chamberlain P F, Rai V, Sargent I L, Redman C W G Wainscoat J S (1997) Presence of foetal DNA in maternal plasma and serum. Lancet 350:485487

Lo Y M D, Fleming K A, Wainscoat J S (1994) Strategies for the detection of autosomal foetal DNA sequence from maternal peripheral blood. Ann NY Acad Sci 731:204–213

Lo Y M D, Patel P, Wainscoat J S, Sampietro M, Gillmer M D G, Fleming K A. Prenatal sex determination by DNA amplification from maternal peripheral blood. Lancet 1989; 2:1363–65.

Lo Y M D, Lo E S F, Watson N, et al. Two-way cell traffic between mother and fetus: biologic and clinical implications. Blood 1996; 88:4390–95.

Lo Y M D, Patel P, Sampietro M, Gilimer M D G, Fleming K A, Wainscoat J S. Detection of single-copy foetal DNA sequence from maternal blood. Lancet 1990; 335:1463–64.

Lo Y M D, Bowell P J, Selinger M, et al. Prenatal determination of foetal RhD status by analysis of peripheral blood of rhesus negative mothers. Lancet 1993; 341:1147–48.

Longo M C, Berninger M S, Hardey J L. Use of uracil DNA glycosylase to control calTy-over contamination in polymerase chain reactions. Gene 1990; 93:125–128.

Mulcahy H E, Croke D T, Farthing M J G. Cancer and mutant DNA in blood plasma. Lancet 1996; 348:628.

Nawroz H, Koch W, Anker P, Stroun M, Sidransky D. Microsatellite alterations in serum DNA of head and neck cancer patients. Nat Med 1996; 2:1035–37.

Rebello M T, Hackett G, Smith J, et al. Extraction of DNA from amniotic fluid cells for the early prenatal diagnosis of genetic disease. Prenat Diagn 1991;11:41–46.

Saiki R K, Gelfand D H, Stoffel S, et al. Primer-directed enzymatic amplification of DNA with a thermostable DNA polymerase. Science 1988; 239:487–91.

Sekizawa A, Watanabe A, T. K, Saito H, Yanaihara T, Sato T. Prenatal diagnosis of the foetal RhD blood type using a single foetal nucleated erythrocyte from maternal blood. Obstet Gynecol 1996; 87:501–505.

Simpson J L, Elias S. Isolating foetal cells from maternal blood: advances in prenatal diagnosis through molecular technology. JAMA 1993; 270:2357–61.

Sohda S, Arinami T, Hamada H, Nakauchi H, Hamaguchi H, The proportion of foetal nucleated red blood cells in maternal blood: estimation by FACS analysis. Prenat Diagn 17:743–752

What is claimed is:

1. A method for detecting a paternally inherited nucleic acid of fetal origin performed on a maternal serum or plasma sample from a pregnant female, which method comprises
   amplifying a paternally inherited nucleic acid from the serum or plasma sample and
   detecting the presence of a paternally inherited nucleic acid of fetal origin in the sample.

2. The method according to claim 1, wherein the foetal nucleic acid is amplified by the polymerase chain reaction.

3. The method according to claim 2, wherein at least one foetal sequence specific oligonucleotide primer is used in the amplification.

4. The method according to claim 1, wherein the foetal nucleic acid is detected by means of a sequence specific probe.

5. The method according to claim 1, wherein the presence of a foetal nucleic acid sequence from the Y chromosome is detected.

6. The method according to claim 5, wherein the Y chromosome sequence is from the DYS14 locus.

7. The method according to claim 5, wherein the Y chromosome sequence is from the SRY gene.

8. The method according to claim 1, wherein the presence of a foetal nucleic acid from a paternally-inherited non-Y chromosome is detected.

9. The method according to claim 8, wherein the non-Y sequence is a blood group antigen gene.

10. The method according to claim 8, wherein the non-Y sequence is a gene which confers a disease phenotype in the foetus.

11. The method according to claim 8, for Rhesus D genotyping a foetus in a Rhesus D negative mother.

12. The method according to claim 5, for determining the sex of the foetus.

13. The method according to claim 5, which comprises determining the concentration of the foetal nucleic acid sequence in the maternal serum or plasma.

14. The method according to claim 13, wherein the determination of the concentration of foetal nucleic acid sequence in the maternal serum or plasma is by quantitative PCR.

15. The method according to claim 13, for the detection of a maternal or foetal condition in which the level of foetal DNA in the maternal serum or plasma is higher or lower than normal.

16. The method according to claim 13, wherein the pattern of variation of foetal DNA concentration in the maternal serum or plasma at particular stages of gestation is different from normal.

17. The method according to claim 13, for detection of pre-eclampsia.

18. The method according to claim 13, for detection of a foetal chromosomal aneuploidy.

19. The method according to claim 1, wherein the sample contains foetal DNA at a fractional concentration of total DNA of at least about 0.14%, without subjecting it to a foetal DNA enrichment step.

20. The method according to claim 19, wherein the fractional concentration of foetal DNA is at least about 0.39%.

21. A method of performing a prenatal diagnosis, which method comprises the steps of:
(i) providing a maternal blood sample;
(ii) separating the sample into a cellular and a non-cellular fraction;
(iii) detecting the presence of a nucleic acid of foetal origin in the non-cellular fraction according to the method of claim 1;
(iv) providing a diagnosis based on the presence and/or quantity and/or sequence of the foetal nucleic acid.

22. The method according to claim 21, wherein the non-cellular fraction as used in step (iii) is a plasma fraction.

23. The method according to claim 21, including performing the further step of allowing clotting in the maternal sample and using the resulting serum in step (iii).

24. A method for detecting a paternally inherited nucleic acid on a maternal blood sample, which method comprises:
removing all or substantially all nucleated and anucleated cell populations from the blood sample,
amplifying a paternally inherited nucleic acid from the remaining fluid and subjecting the amplified nucleic acid to a test for the Paternally inherited fetal nucleic acid.

25. A method for performing a prenatal diagnosis on a maternal blood sample, which method comprises
obtaining a non-cellular fraction of the blood sample
amplifying a paternally inherited nucleic acid from the non-cellular fraction
and performing nucleic acid analysis on the amplified nucleic acid to detect paternally inherited fetal nucleic acid.

26. The method according to claim 9, wherein the blood group antigen gene is the rhesus D gene.

27. The method according to claim 10, wherein the gene is the rhesus D gene.

* * * * *